(12) United States Patent
Abuknesha

(10) Patent No.: US 6,225,043 B1
(45) Date of Patent: *May 1, 2001

(54) SEPARATION AND ANALYSIS

(75) Inventor: Ramadan Arbi Abuknesha, London (GB)

(73) Assignee: Gec-Marconi Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/700,121

(22) Filed: Aug. 20, 1996

Related U.S. Application Data

(63) Continuation of application No. 08/310,036, filed on Sep. 21, 1994, now abandoned, which is a continuation of application No. 07/962,935, filed on Oct. 19, 1992, now abandoned.

(30) Foreign Application Priority Data

Oct. 18, 1991 (GB) .................................................. 9122180

(51) Int. Cl.$^7$ .............................. C12Q 1/00; G01N 33/53
(52) U.S. Cl. .............................. 435/4; 435/7.72; 435/7.8; 435/7.91; 435/7.92; 435/961; 435/975; 435/283.1; 436/518; 436/536; 436/538; 436/541
(58) Field of Search .................................... 435/7.32, 7.5, 435/7.8, 7.71, 7.72, 7.91, 7.92, 971, 961, 4, 283.1; 436/536, 538, 518, 541

(56) References Cited

U.S. PATENT DOCUMENTS

| | | | |
|---|---|---|---|
| 4,506,009 | * | 3/1985 | Lenhoff .................. 435/7.1 |
| 4,668,621 | * | 5/1987 | Doellgast ................. 435/13 |
| 4,749,647 | * | 6/1988 | Thomas ................... 435/6 |
| 4,904,583 | * | 2/1990 | Mapes ..................... 435/7.1 |
| 4,935,339 | * | 6/1990 | Zahradnik ................ 435/5 |
| 5,043,288 | * | 8/1991 | Motsenbocker .......... 436/518 |
| 5,357,040 | * | 10/1994 | Matsueda et al. . |

FOREIGN PATENT DOCUMENTS

| | | |
|---|---|---|
| 0152254 | 8/1985 | (EP) . |
| 0177191 | * 4/1986 | (EP) . |
| 0245926 | 5/1988 | (EP) . |
| 0 310 413 A2 | 4/1989 | (EP) . |
| 0313274 | 4/1989 | (EP) . |
| 0378204 | 7/1990 | (EP) . |
| 2032619 | 5/1980 | (GB) . |
| 2171999 | 9/1986 | (GB) . |
| WO92/16838 | 10/1992 | (WO) . |

OTHER PUBLICATIONS

Milstein et al (Nature vol. 305 Oct. 6, 1983 pp 537–540).*
Rattle etal "New Separation Method for Monoclonal Immunoradiometric Assays and Its Application to Assays for Thyrotropin & Human Choriogoradotropin" Clin. Chem. 30/9, 1457–1461 (1984).*

* cited by examiner

*Primary Examiner*—Patricia A. Duffy
(74) *Attorney, Agent, or Firm*—Kirschstein, et al.

(57) ABSTRACT

A separation method, a method for detection, a sensor, and a test-kit find application in immunological detection. The separation method provides for separation of a primary species which separation method is suitable for use in an immunoassay method for the detection of an analyte species and includes the use of a first auxiliary species capable of being formed into a second auxiliary species which second auxiliary species is capable of interacting with a third species to facilitate separation.

16 Claims, No Drawings

SEPARATION AND ANALYSIS

CROSS REFERENCE TO RELATED APPLICATION

This application is a continuation of application Ser. No. 08/310,036, filed Sep. 21, 1994, now abandoned, which was a continuation of application Ser. No. 07/962,935 filed Oct. 19, 1992, now abandoned.

BACKGROUND OF THE INVENTION

The present invention relates to a separation method, to a method for detection, to a sensor, and to a test-kit which find application in immunological detection.

SUMMARY OF THE INVENTION

According to one aspect of the present invention there is provided a separation method for separation of a primary species which separation method is suitable for use in an immunoassay method for the detection of an analyte species and includes the use of a first auxiliary species capable of being formed into a second auxiliary species which second auxiliary species is capable of interacting with a third species to facilitate separation.

In one embodiment of the present invention the separation method also includes the steps of forming the second auxiliary species from the first auxiliary species, and allowing the second auxiliary species and the third species to react so as to facilitate separation.

According to another aspect of the present invention there is provided a method for the detection of an analyte species by immunoassay which method includes a separation method for separation of a primary species which separation method includes the use of a first auxiliary species capable of being formed into a second auxiliary species which second auxiliary species is capable of interacting with a third species to facilitate separation.

In another embodiment of the present invention there is provided a method for the detection of an analyte species by immunoassay which method comprises allowing a primary immune reaction to take place, subsequently forming the first auxiliary species into the second auxiliary species and allowing the second auxiliary species to react with the third species to facilitate a separation step in the immunoassay.

According to a further aspect of the present invention there is provided a sensor suitable for use in the detection of an analyte species by immunological detection which sensor is constructed such as to permit the performance of a separation method for separation of a primary species, or a method for detection which method for detection includes a separation method for separation of a primary species, which includes the use of a first auxiliary species capable of being formed into a second auxiliary species which second auxiliary species is capable of interacting with a third species to facilitate separation.

According to yet a further aspect of the present invention there is provided a test-kit for performing a method of detection, which method includes a separation method for separation of a primary species, in accordance with the present invention which test-kit includes a first auxiliary species capable of being formed into a second auxiliary species which second auxiliary species is capable of interacting with a third species to effect a separation.

The second auxiliary species may be, for example, a ligand. Where the second auxiliary species is a ligand the third species may be, for example, a binder species for the ligand.

The first auxiliary species and the second auxiliary species may be considered to be "auxiliary" in the sense that neither of these species takes part in a primary immune reaction. Thus, the first auxiliary species and the second auxiliary species may be considered as not being primary species. It is to be understood that a primary species in accordance with the present invention is a species which may take part in a primary immune reaction.

By way of example, a primary immune reaction (which may also be described as a primary immune binding reaction) is one in which an analyte species undergoes a specific binding reaction or an authentic analyte species (as hereinafter defined) undergoes a specific binding reaction, or an analyte species and an authentic analyte species undergo specific binding reactions. (It will be appreciated that the analyte species and the authentic analyte species undergo specific binding reactions with other species and not with each other.)

By way of example, a primary species may be a primary antibody or a ligand (e.g. an antigen). It is to be understood that, for example, a primary species may be an antibody to an analyte species, or an antibody to an authentic analyte species; it will be appreciated that, for a given immunoassay, the antibody to the analyte species and the antibody to the authentic analyte species will be the same antibody.

It is also to be understood that a primary species may be, for example, an analyte species or an authentic analyte species.

By way of example, it is possible to choose a third species which is a species which does not take part in a primary immune reaction; such a third species may be regarded as a third auxiliary species. For example, a third species being a third auxiliary species may be associated with a primary species (as further disclosed hereinafter) or provided on a support material (as further disclosed hereinafter).

Alternatively, by way of example, a third species may be chosen such as to have a part which provides a species for interaction with the second auxiliary species and a part which provides a primary species being a binder for a primary species; an example of such a third species is an antibody having more than one function (e.g. a bifunctional antibody). It is to be understood that where, for example, a third species has a part which provides a species for interaction with the second auxiliary species, that part may be regarded as an "auxiliary function" in that it may interact with the second auxiliary species. It is also to be understood that where, for example, a third species is a species which has an auxiliary function and itself has a part which provides a primary species, the third species may be regarded as a primary species in that it has a part which provides a primary species.

By way of example, where the third species is an antibody to the second auxiliary species the third species may be considered, by way of example, to be an "anti-second auxiliary species agent".

The first auxiliary species may be, for example, regarded as a precursor for the second auxiliary species. For example, the first auxiliary species may be formed into the second auxiliary species by means of chemical synthesis. Alternatively, by way of example, the first auxiliary species may be essentially similar to the second auxiliary species with the exception that the first auxiliary species carries a "blocking" entity which inhibits the capability of the second auxiliary species to interact (e.g. react) with the third species. On removal of the blocking entity (i.e. the "unblocking" of the second auxiliary entity) the first auxiliary species is formed into the second auxiliary species which is then capable of interacting (e.g. reacting) with the third species.

It is to be understood that the removal of a blocking entity may be considered to be "unmasking" of a "masked" auxiliary species or the "switching on" of an interacting (e.g. reacting) capability of an auxiliary species.

Also, for example, any suitable structural change may be utilised in accordance with the present invention to obtain the second auxiliary species from the first auxiliary species.

By way of example, any substance (e.g. an organic substance) which can act as a ligand, and which can exist in more than one stable form or structure may be suitable to provide a first auxiliary species and a second auxiliary species in accordance with the present invention.

Thus, by way of example, to obtain a second auxiliary species being a ligand any suitable first auxiliary species (which may be considered to be a pro-ligand) capable of forming the ligand may be utilised.

For example, an antigenic ligand (e.g. a hapten) may be selected as the second auxiliary species and antibodies (either monoclonal or polyclonal) to the ligand may be raised (e.g. in any suitable manner such as those known in the art) said antibodies being a binder species forming the third species for reacting with the second auxiliary species.

The second auxiliary species may be formed from the first auxiliary species by any suitable means, for example by chemical means or biochemical (e.g. enzymatic) means.

It is to be understood that formation of the second auxiliary species from the first auxiliary species may be effected in any suitable manner (i.e. "switching on" of an interacting (e.g. reacting) capability of an auxiliary species may be effected in any suitable manner), for example, by adding to a first auxiliary species, or by removing something from a first auxiliary species, or by exposing a ligand (e.g. an antigenic determinant) of a first auxiliary species (e.g. by a conformational change).

Preferably any affinity of the first auxiliary species for the third species is much lower (e.g. three-fold lower and preferably 1% or lower) than affinity between the second auxiliary species and the third species.

The first auxiliary species may be chosen or arranged such as to have stability which is satisfactory under conditions involved in its storage and use.

A second auxiliary species and a third species in accordance with the present invention may be, for example, any suitable ligand-binder species pair, the ligand being the second auxiliary species and the binder species being the third species. Examples of ligand-binder species pairs are antigen-antibody pairs, non-antigenic ligand-binder species pairs and co-factor-protein pairs.

By way of example, any suitable ligand may be utilised as a second auxiliary species, examples of which ligands are antigenic ligands (such as haptens) and non-antigenic ligands.

Examples of antigenic ligands are 2,4 dinitrophenol, fluorescein, digitoxin, coumarin, and cibacron blue. Examples of non-antigenic ligands are ligands of specific ligand-binder species pairs (e.g. the ligand biotin in the case of the specific ligand-binder species pair biotin-avidin).

By way of example, any suitable binder species may be utilised as a third species; the binder species may be, for example, a binding protein (e.g. an antibody or a binder partner for a ligand).

Thus, for example, where the second auxiliary species is an antigenic ligand the binder species may be an antibody to the ligand.

Accordingly, where, for example, the second auxiliary species is 2,4 dinitrophenol, fluorescein, digitoxin, coumarin, or cibacron blue, the binder species may be, respectively, anti-2,4 dinitrophenol antibody, anti-fluorescein antibody, anti-digitoxin antibody, anti-coumarin antibody, or anti-cibacron blue antibody.

Where, for example, the second auxiliary species is a non-antigenic ligand, the ligand may be, for example, such that the binder species is a binding partner that is a non-imunoglobulin (e.g. a naturally-occurring protein); the binding partner may be considered to be the binder of the ligand. An example of such a binding partner is avidin in the specific ligand-binder species pair comprising a biotin-avidin complex.

A separation method in accordance with the present invention may therefore, for example, utilise separation systems comprising 2,4 dinitrophenol/anti-2,4 dinitrophenol antibody, fluorescein/anti-fluorescein antibody, digitoxin/anti-digitoxin antibody, coumarin/anti-coumarin antibody, cibacron blue/anti-cibacron blue antibody or a biotin-avidin complex.

The second auxiliary species may be formed from the first auxiliary species in any suitable manner as hereinbefore disclosed. For example the first auxiliary species may be an enzyme substrate (e.g. a substrate for a hydrolase) which may be converted, enzymatically, into constituents or product fragments which may act as the second auxiliary species. An enzyme substrate and constituents produced by enzymatic action may be arranged, for example, to differ structurally so as to have large differences in affinity for the third species.

Examples of enzymes suitable for use in an enzyme/enzyme substrate system are glactosidases, glucosidases and phosphatases; thus, for example, galactosyl-7-hydroxy coumarin may be formed into galactose+7-hydroxy coumarin, or glucosyl-7-hydroxy coumarin may be formed into glucose+7-hydroxy coumarin, or phosphate-7-hydroxy coumarin may be formed into phosphate+7-hydroxy coumarin. By way of further example, an enzyme/enzyme substrate system which yields nitrophenol (e.g. by conversion of nitrophenol derivatives) may be used. In the immediately foregoing examples it will be appreciated that the enzymatic substrates constitute first auxiliary species (being ligand precursors) and the ligands 7-hydroxy coumarin and nitrophenol constitute second auxiliary species.

By way of further example, a co-factor system such as Cofactor 1→Cofactor II may be utilised in accordance with the present invention to provide a first auxiliary species and a second auxiliary species. Thus, for example, NAD→NADH or NADP→NAD may be utilised.

Also, by way of example a system involving reduced chromophore dye oxidised chromophore dye may be utilised in accordance with the present invention to provide a first auxiliary species and a second auxiliary species.

Examples of further systems which may be used to produce a first auxiliary species and a second auxiliary species are ultraviolet (UV) light-sensitive precursor substances that may be influenced by photolysis and chelating agent/chelate-metal complex systems.

By way of example, any desired auxiliary species utilised in an immunological procedure, in accordance with the present invention, may, optionally, be provided on a support material. For example, if desired, a first auxiliary species, or a second auxiliary species or a third auxiliary species may be provided on a support material. By way of example the support material itself may provide a first auxiliary species or a second auxiliary species, or the support material may have attached thereto, either directly or indirectly, a first auxiliary species, or a second auxiliary species, or a third auxiliary species.

Thus, in this specification "provided on a support material" when used in relation to a first auxiliary species, a second auxiliary species or a third auxiliary species, embraces situations where the support material itself provides a first auxiliary species or a second auxiliary species, and situations where the support material has attached thereto (for example immobilised thereon), either directly or indirectly, a first auxiliary species, or a second auxiliary species, or a third auxiliary species. Thus, for example, a first auxiliary species or a second auxiliary species may be provided by chemical groups or units of the support material, or a first auxiliary species, or a second auxiliary species, or a third auxiliary species may be, for example, attached to the support material by any suitable means (e.g. by covalent linkage or adsorption). Where the support material is, for example, a polymer, units of the polymer may act as a first auxiliary species or a second auxiliary species. Also, by way of example, surface groups present on a support material, such as polystyrene or modified silica, may act as a first auxiliary species or a second auxiliary species.

By way of example, the support material may, if desired, provide oligomers or polymers of first auxiliary species, second auxiliary species or third auxiliary species.

Where a first auxiliary species, or a second auxiliary species or a third auxiliary species is attached to a support material the first auxiliary species or second auxiliary species or third auxiliary species may be directly attached to the support material or indirectly attached to the support material via other species (e.g. a carrier protein).

In one embodiment the present invention provides a method which also includes the step of attaching, either directly, or indirectly, a first auxiliary species, or a second auxiliary species or a third auxiliary species to a support material.

By way of further example, the surface of a support material may be activated thereby to permit attachment of a first auxiliary species or a second auxiliary species or a third auxiliary species; for example, the surface of a suitable support material may be activated by chemical treatment to provide free amino groups to which a first auxiliary species, or a second auxiliary species or a third auxiliary species may be linked.

Further, by way of example, instead of linking single first auxiliary species or single second auxiliary species or single third auxiliary species to free amino groups, (produced as immediately hereinbefore disclosed) oligomers or polymers of first auxiliary species, or second auxiliary species or third auxiliary species may be attached directly or indirectly to a support material.

Thus, for example, oligomers or polymers of a first auxiliary species, or of a second auxiliary species or of a third auxiliary species may be attached (e.g. via free amino groups) to a support material.

Also, by way of example, a first auxiliary species or a second auxiliary species or a third auxiliary species may be linked (e.g. covalently or otherwise) to a further species (e.g. a carrier protein or a polymer) and the further species may be associated, by any suitable means (e.g. adsorption, covalent linking or by use of a further ligand-binder pair), with the support material such that the first auxiliary species, or the second auxiliary species or the third auxiliary species may become indirectly provided on the support material.

By way of further example, instead of linking single first auxiliary species, or single second auxiliary species or single third auxiliary species indirectly to a support material it is possible to link (e.g. covalently or otherwise) oligomers or polymers of such species to a further species (e.g. a carrier protein or a polymer) and the further species may be associated, by any suitable means (e.g. adsorption, covalent linking or by use of a further ligand-binder pair), with the support material such that oligomers or polymers of first auxiliary species or second auxiliary species or third auxiliary species may become indirectly provided on the support material.

It is to be understood that where a second auxiliary species is initially provided on a support material, said second auxiliary species may be treated to convert it to the first auxiliary species ready for use in accordance with the present invention.

Examples of support materials which may find application in accordance with the present invention (e.g. which may have attached thereto, either directly or indirectly, a first auxiliary species, a second auxiliary species, or a third auxiliary species) are solid phase materials such as a reaction vessel wall, insoluble polysaccharides (which may be in particulate form), microparticles (e.g. particulate microcellulose), insoluble polysaccharides with entrapped iron oxide (e.g. magnetisable particles such as magnetisable micro-particulate materials), polystyrene (e.g. in the form of beads, tubes, wells, microtitre plates, discs, or dip-sticks), cross-linked dextran (e.g. Sephadex), insoluble polymer structures, glass surfaces (e.g. of an immunosensor device), derivatised silica surfaces (e.g. having silyl groups with chemical functions attached), soluble polymers attached to a suitable support (e.g. a glass surface such as a fibre-optic surface), nylon, or a polyamide. The support material may be, for example, a surface of a reaction vessel.

In view of the foregoing disclosure it will be appreciated that a support material may provide, for example, a first auxiliary species comprising an enzyme substrate, or an enzyme co-factor, or a UV sensitive entity, or a chelating agent for forming, with a metal, a metal chelate, or a reduced chromophore dye, which first auxiliary species may be treated, respectively, enzymatically, or by UV irradiation, or with metal ions, or by oxidising conditions, to give a second auxiliary species which is capable of reaction with the third species.

The present invention may find application in the detection of analyte species in any suitable sample. Thus, for example, samples of water, soil, living species (such as plants (e.g. vegetables) or animals) or air may provide an analyte species for detection in accordance with the present invention. Examples of biological samples in which an analyte species may be detected in accordance with the present invention are blood, plasma, serum, urine, saliva and milk. An analyte species may be, for example, present in water, an aqueous preparation or a fluid extract. An analyte species may be, for example, a ligand (e.g. a hapten) or a binder (e.g. an antibody).

Examples of analyte species which may be detected in accordance with the present invention are:
 (a) steroid hormones such as progesterone, 17 α-hydroxy progesterone, and estradiol (e.g. in a sample of blood, serum, saliva, urine or milk),
 (b) hormones such as thyroid hormone (e.g. thyroxine or triiodothyronine),
 (c) steroids in extracts (e.g. extracts of solids or liquids),
 (d) drugs (such as drugs of abuse (e.g. phenobarbital) or therapeutic drugs (e.g. dioxin)) in for example a sample of blood, serum, saliva or urine, (e) polypeptide hormones (e.g. hCG) in, for example, a sample of blood or urine, (f) tumour markers such as marker proteins (e.g. in a sample of blood or serum), (g) protein antigens, (h) blood proteins (e.g. human serum albumin, immunoglobulins (e.g. IgG), enzyme markers or receptors), (i) marker proteins for tissue or organ disease, (j) pesticides such as insecticides, or herbicides (e.g. in a sample of water or soil), (k) toxins (such as those extracted from feeds and food stuffs), (l) micro-organisms (e.g. viruses and bacteria) and (m) antibodies to micro-organisms.

Further examples of analyte species which may be detected in accordance with the present invention are complexes of metals.

Thus, the present invention may find application in, for example, the detection of complexes of metals such as strong metal complexes which may be regarded as toxic (e.g. in biological terms when present in the environment).

An example of a metal complex which may be detected in accordance with the present invention is methyl mercury.

By way of further example, metal ions may be formed into a complex of a metal by use of a complexing agent (e.g. a chelating agent) and the complex thus formed may act as an analyte species in accordance with the present invention. Thus, for example, the present invention may find application in the detection of metal ions.

It is to be understood that when a metal complex is to be detected in accordance with the present invention then, for example, use may be made of an antibody to the metal complex.

It will be appreciated that the present invention may be utilised in qualitative analysis, which may also be considered to be qualitative detection, of an analyte species or in quantitative analysis, which may also be considered to be quantitative detection (i.e. measurement or determination), of an analyte species.

By way of example, the present invention may be applied in any immunological procedure or sensor wherein a separation of bound and unbound fractions of a tracer species (which may also be considered to be a labelling species) is required. Such procedures and sensors include competitive immunoassay procedures (e.g. heterogeneous antigen-labelled immunoassays, or heterogeneous antibody-labelled immunoassays, for small or large molecular weight substances), non-competitive immunoassay procedures (e.g. heterogeneous assays for large molecular weight substances or micro-organisms where immobilisation by an antibody is required), and all types of immunosensor devices where an immune reaction species is required to be associated with a surface of an immunosensor device (e.g. a device which has an optical mode of detection (i.e. gives an optical signal) or an electro-chemical mode of detection (e.g. gives an electrical signal)).

Any suitable detectable species or tracer species may be used in accordance with the present invention.

Examples of tracer species are: enzymes (e.g. alkaline phosphatase, β-galactosidase, or horse-radish peroxidase), fluorophores (e.g. fluoresceins, coumarins or rhodamine), chemiluminescent compounds, bioluminescent compounds, radioisotopes and dyes.

The present invention may be utilised substantially to overcome or avoid disadvantages of known types of immunological procedures: thus, for example, in certain known types of immunoassay which require the use of a primary species, comprising an antigen or an antibody, attached to a support material in order to permit separation of bound and unbound fraction of tracer species, it is often necessary to add support material during the assay; this may prove to be inconvenient from the point-of-view of handling and fast addition of support material in some assays and thus may present a disadvantage. Also, for example, the use of support materials may present problems in automated systems. Furthermore, where, for example, a primary antibody is immobilised on a support material any immunological reaction between the primary antibody and an analyte species or authentic analyte species (as hereinafter defined) carrying a tracer or any other species may be slow to approach equilibrium or any other desired point in the reaction (i.e. a primary immune reaction may be slow to proceed to equilibrium or any other desired point in the reaction).

Similar disadvantages may be encountered in situations where an immobilised antigen (e.g. an immobilised authentic analyte species) is used in effecting a primary immune reaction.

In accordance with one embodiment of the present invention a primary immune reaction may be allowed to proceed to equilibrium, or any other desired point in the reaction, in solution so that the reaction is not inhibited by involving immobilised species. Subsequently, in accordance with an embodiment of the present invention, at a chosen time, the second auxiliary species may be formed from a first auxiliary species provided on a support material such that attachment to the support material may occur (i.e. the reactive capability of an auxiliary species provided on the support material may be "switched on "). Thus, for example, an appropriate species involved in the primary immune reaction may be attached to a support material.

Where a third species is associated with a primary species (e.g. a primary antibody or an antigen), it is to be understood that attachment to a support material may be effected, by way of example, as a consequence of the reaction (e.g. binding) of the second auxiliary species (produced from the first auxiliary species) on the support material with the third species which is associated with the primary species; also it is to be understood that the formation of the second auxiliary species from the first auxiliary species may be regarded as "switching on" the reactive capability of species provided on the support material. Thus, for example, where a ligand-binder pair is utilised in accordance with the present invention and this involves the use of antigenic sites then the present invention may be regarded as utilising "switchable" antigenic sites.

In accordance with another embodiment of the present invention a primary immune reaction may be allowed to proceed to equilibrium, or any other desired point in the reaction, in solution so that the reaction is not inhibited by involving immobilised species. Subsequently, in accordance with an embodiment of the present invention, at a chosen time, the second auxiliary species may be formed from a first auxiliary species associated with a primary species (i.e. the reactive capability of an auxiliary species associated with a primary species is "switched on "). Thus, for example, an appropriate species involved in the primary immune reaction may be attached to support material.

Where a first auxiliary species is associated with a primary species (e.g. a primary antibody or an antigen) it is to be understood that attachment to a support material may be effected, by way of example, as a consequence of the reaction (e.g. binding) of the second auxiliary species (produced from the first auxiliary species) with a third auxiliary species which is provided on a support material; also it is to be understood that the formation of the second auxiliary species from the first auxiliary species may be regarded as "switching on" the reactive capability of species.

It is to be understood that where a third species does not have a part which provides a primary species being a binder for a primary species, the third species will be a third auxiliary species and it may be associated with a primary species by a suitable linkage. Also, it is to be understood that where a third species is provided on a support material, the third species may be regarded as a third auxiliary species.

By way of example, primary species may be associated with single first auxiliary species or with an oligomer or a polymer of a first auxiliary species.

Alternatively, by way of example, a primary species may be associated with a single third species or with an oligomer or a polymer of a third species.

A first auxiliary species (or a second auxiliary species formed therefrom) or a third species may be associated with a primary species by any suitable linkage; such a linkage may include a non-specific binding link or links (e.g. a covalent link or links or adsorption) or a specific binding link or links, or any combination of such links.

Since, in accordance with the present invention, a primary immune reaction may proceed in solution the reaction may thus be faster than in prior art methods and, since the support material may be present throughout the reaction, it is not necessary to add solid materials during an assay.

By delaying attachment of species to a support material until a primary immune reaction has occurred in accordance with the present invention, speed, sensitivity and precision of an immunoassay procedure, for example, may be improved. (It will be appreciated that an immunoassay procedure may need to have a sensitivity such that femtomolar or picomolar concentrations of analyte species may be detected.)

In one form of a known assay procedure known as enzyme labelled immunosorbent assay (ELISA) a surface of an assay vessel (e.g. a surface of a well or a microtitre plate) is used to adsorb an assay constituent so that a separation step may be effected. Incubation times using such an assay procedure range from 2 to 24 hours with total assay times of from 4 to 24 hours; these times may be reduced by use of the present invention. Thus, for example, the present invention may find one application in enzyme labelled immunosorbent assay.

The formation of the second auxiliary species may be effected, for example, by the addition of a suitable reagent or the introduction of energy.

Thus, for example, the second auxiliary species may be formed from the first auxiliary species by means of enzymes, chemical reagents or external influences such as light sources (e.g. such as UV). By way of further example, a pH change, or the addition of a chemical solution (e.g. containing metal ions) may be used to form the second auxiliary species.

It will be appreciated that the present invention may be used to control or delay initiation of separation until a desired time after initiation of a primary immune reaction.

It is also to be appreciated that the first auxiliary species, capable of being formed into the second auxiliary species, need not be provided on a support material since, for example, any chosen auxiliary species involved in an immunoassay may be provided on a support material; this is further disclosed hereinafter.

It is to be understood that an "authentic analyte species" is a species which is capable of reacting in a substantially similar manner as an analyte species to be detected under substantially similar conditions; for example, an authentic analyte species may be an antigen (e.g. a derivative of an analyte species) which will bind to an antibody to be used in an assay in substantially the same manner as an analyte species to be detected.

It will be appreciated that an authentic analyte species may be used, inter alia, as a calibrator or a standard.

By way of example, where circumstances permit, a tracer species (which may also be considered to be a labelling species) may act as a tracer species or labelling species and also act as a means for forming the first auxiliary species into the second auxiliary species.

Thus, for example, where circumstances permit and a tracer species or a labelling species is an enzyme, the enzyme may act as a tracer or labelling species and also act to effect enzymatic conversion of the first auxiliary species into the second auxiliary species (i.e. formation of the second auxiliary species from the first auxiliary species).

Therefore, it is to be understood that, for example, in addition to providing a tracer or labelling species, a tracer or labelling species may be utilised to "switch on" an interactive (e.g. reactive) capability of the first auxiliary species.

By way of example, a galactosidase (e.g. β-galactosidase) or an alkaline phosphatase may be used to form a ligand from a precursor therefor (i.e. a pro-ligand) comprising, respectively, a galactosidase coumarin or a phosphate coumarin.

From the foregoing disclosure it will be appreciated that, for example, a first auxiliary species (e.g. a pro-ligand) may be treated with a reagent or reagents for forming the second auxiliary species from the first auxiliary species after a reagent (or reagents) for effecting other interactions (e.g. a primary immune reaction) has (or have) been allowed to react for a desired period of time.

However, where circumstances permit, a reagent or reagents for forming the second auxiliary species from the first auxiliary species may be used, for example, simultaneously with a reagent or reagents for effecting other interactions (e.g. a primary immune reaction).

For example, where a first auxiliary species (e.g. a ligand) is carried on a support material a reagent or reagents for forming the second auxiliary species from the first auxiliary species (i.e. a reagent or reagents capable of "switching on" an interactive (e.g. a reactive) capability of the first auxiliary species) and a reagent or reagents for effecting other interactions (e.g. a primary immune reaction) may be applied simultaneously. The other interactions (e.g. a primary immune reaction) may take place in solution (and thus relatively swiftly) whereas the formation of the second auxiliary species from the first auxiliary species on the support material may take place relatively slowly, for example due to the fact that the first auxiliary species is associated with a support material. Thus, for example, in some circumstances benefits of relatively swift reaction in solution followed by "switching on" of a separation process may be achieved whilst still preserving the facility of bringing together some, most, or all, necessary reagents at the same time.

The present invention will now be further described by reference to examples of configurations of immunoassay methods utilising the invention. Thus:

(A) By way of example, the present invention may involve the use of:
   (i) a support material providing a precursor for a ligand,
   (ii) an authentic analyte species conjugated with a binder species for the ligand (e.g. an antibody to the ligand), and (iii) a tracer species (as hereinafter described) conjugated to an analyte binding species (e.g. a primary antibody) (i.e. a species which will bind with the authentic analyte species or an analyte species).

It will be appreciated that, in this example, the precursor for a ligand is a first auxiliary species and that a ligand is a second auxiliary species; also, it will be appreciated that the binder species for the ligand is a third species, being in this example, a third auxiliary species.

In carrying out an assay, a primary immune reaction may be allowed to take place by permitting authentic analyte species conjugated to the binder species to compete with analyte species, if any, in a sample (e.g. an "unknown" amount or a "known" (or "standard ") amount), for binding with the analyte binding species conjugated with the tracer species. When the primary immune reaction has proceeded to a desired point (e.g. equilibrium), the precursor for the ligand is converted to the ligand such that binding may occur between the ligand and the binder species with the result that any tracer species associated with the binder species (by binding between the authentic analyte species and the analyte binding species) will become attached to the support material.

Any tracer species associated with the support material may be detected in any suitable manner such as those known in the art or by any suitable means such as those known in the art.

It will be appreciated that "unknown" as used in this Specification with reference to an amount of an analyte species means an unknown amount to be detected in a sample; also it will be appreciated that "known" or "standard" as used in this specification with reference to an amount of an analyte species means a known or standard amount of an analyte species such as may be provided, for example, by a standard analyte species solution.

It will also be appreciated that, in this example, in the presence of no analyte species in a sample the amount of tracer species which may be attached to a support material after carrying out an assay in accordance with the present invention may represent a maximum amount; the amount of tracer species which may be attached to a support material will decrease as the amount of analyte species in a sample increases.

By use of calibration curves, obtained using a range of samples containing known amounts of standard analyte species, the amount of analyte species in an "unknown" sample may be determined.

(B) By way of further example, the present invention may involve the use of:
  (i) a support material providing a precursor for a ligand,
  (ii) a hybrid comprising a binder species for the ligand (e.g. an antibody to the ligand) conjugated with an analyte binding species (e.g. a primary antibody), and
  (iii) an authentic analyte species conjugated to a tracer.

It will be appreciated that, in this example, the precursor for a ligand is a first auxiliary species and that a ligand is a second auxiliary species; also it will be appreciated that the binder species for the ligand is a third species, in this example a third auxiliary species.

In carrying out an assay, a primary immune reaction may be allowed to take place by permitting authentic analyte species, conjugated with the tracer species, to compete with analyte species, if any, in a sample (e.g. an "unknown" amount or a "known" (or "standard ") amount), for binding with the analyte binding species. When the primary immune reaction has proceeded to a desired point (e.g. equilibrium), the precursor for the ligand is converted into the ligand such that binding occurs between the ligand and the binder species with the result that any tracer species associated with the binder species (by binding between the authentic analyte species and the analyte binding species) will become attached to the support material.

Any tracer species associated with the support material may be detected in any suitable manner such as those known in the art or by any suitable means such as those known in the art.

It will be appreciated that, in this example, in the presence of no analyte species in a sample the amount of tracer species which may be attached to a support material after carrying out an assay in accordance with the present invention may represent a maximum amount; the amount of tracer species which may be attached to a support material will decrease as the amount of analyte species in a sample increases.

By use of calibration curves, obtained using a range of samples containing known amounts of standard analyte species, the amount of analyte species in an "unknown" sample may be determined.

(C) By way of further example, the present invention may involve the use of:
  (i) an authentic analyte species conjugated to a precursor for a ligand,
  (ii) an analyte binding species (e.g. a primary antibody) conjugated to a tracer species, and
  (iii) a support material providing a binder species for the ligand.

It will be appreciated that, in this example, the precursor for the ligand is a first auxiliary species and that a ligand is a second auxiliary species; also it will be appreciated that the binder species is a third species, being in this example, a third auxiliary species.

In carrying out an assay, a primary immune reaction may be allowed to take place by permitting authentic analyte species, conjugated to the precursor for the ligand, to compete with analyte species, if any, in a sample (e.g. an "unknown " amount of a "known" (or "standard ") amount), for binding with the analyte binding species, conjugated to the tracer species. When the primary immune reaction has proceeded to a desired point (e.g. equilibrium), the precursor for the ligand is converted into the ligand such that binding occurs between the ligand and the binder species with the result that any tracer species associated with the ligand (by binding between the authentic analyte species and the analyte binding species) will become attached to the support material.

Any tracer species associated with the support material may be detected in any suitable manner such as those known in the art or by any suitable means as those known in the art.

It will be appreciated that, in this example, the presence of no analyte species in a sample the amount of tracer species which may be attached to a support material after carrying out an assay in accordance with the present invention may represent a maximum amount; the amount of tracer species which may be attached to a support material will decrease as the amount of analyte species in a sample increases.

By use of calibration curves, obtained using a range of samples containing known amounts of standard analyte species, the amount of analyte species in an "unknown" sample may be determined.

(D) By way of further example, the present invention may involve the use of:
  (i) a precursor for a ligand conjugated to an analyte binding species (e.g. a primary antibody), (ii) an authentic analyte species conjugated to a tracer species, and (iii) a support material providing a binder species for the ligand.

It will be appreciated that, in this example, the precursor for a ligand is a first auxiliary species and that a ligand is a second auxiliary species; also it will be appreciated that the binder species is a third species, in this example a third auxiliary species.

In carrying out an assay, a primary immune reaction may be allowed to take place by permitting authentic analyte species, conjugated to the tracer species, to compete with analyte species, if any, in a sample (e.g. an "unknown" amount or a "known" (or "standard") amount), for binding with the analyte binding species, conjugated to the precursor for the ligand. When the primary immune reaction has proceeded to a desired point (e.g. equilibrium), the precursor for the ligand is converted to the ligand such that binding occurs between the ligand and the binder species with the result that any tracer species associated with the ligand (by binding between the analyte binding species and the authentic analyte species) will become attached to the support material.

Any tracer species associated with the support material may be detected in any suitable manner such as those known in the art or by any suitable means as those known in the art.

It will be appreciated that, in this example, in the presence of no analyte species in a sample the amount of tracer species which may be attached to a support material after carrying out an assay in accordance with the present invention may represent a maximum amount; the amount of tracer species which may be attached to a support material will decrease as the amount of analyte species in a sample increases.

By use of calibration curves, obtained using a range of samples containing known amounts of standard analyte species, the amount of analyte species in an "unknown" sample may be determined.

(E) By way of further example, the present invention may involve the use of:

(i) a precursor for a ligand conjugated to a first analyte binding species (e.g. a first antibody to the analyte species), (ii) a tracer species conjugated to a second analyte binding species (e.g. a second antibody to the analyte species), and (iii) a support material providing a binder species for the ligand.

It will be appreciated that, in this example, the precursor for a ligand is a first auxiliary species and that a ligand is a second auxiliary species; also it will be appreciated that the binder is a third species, in this example a third auxiliary species.

In carrying out an assay, a primary immune reaction may be allowed to take place by permitting the first analyte binding species to bind with analyte species, if any, in a sample (e.g. an "unknown" amount or a "known" (or "standard") amount), and allowing second analyte binding species to bind with any analyte species.

When the primary immune reaction has proceeded to a desired point (e.g. equilibrium), the precursor for the ligand is converted into the ligand such that binding occurs between the ligand and the binder species for the ligand such that binding occurs between the ligand and the binder species with the result that any tracer species associated with the ligand (by binding between the first analyte binding species and any analyte species (bound by the first analyte binding species) and the second analyte binding species) will become attached to the support material.

Any tracer species associated with the support material may be detected in any suitable manner as those known in the art or by any suitable means such as those known in the art.

It will be appreciated that, in this example, in the presence of no analyte species in a sample, substantially no tracer species will become attached to the support material because there is no analyte species to form a "bridge" between the first analyte binding species and the second analyte binding species. However, as the concentration of an analyte species in a sample increases, then the amount of tracer species attached to the support material increases.

By use of calibration curves, obtained using a range of samples containing known amounts of standard analyte species, the amount of analyte species in an "unknown" sample may be determined.

By way of further example, (i), (ii) and (iii) of E hereinbefore disclosed may be utilised in an alternative manner.

Thus, for example, a primary immune reaction may be allowed to take place by permitting the first analyte binding species to bind with analyte species, if any, in a sample (e.g. an "unknown" amount or a "known" (or "standard") amount). When the primary immune reaction has proceeded to a desired point (e.g. equilibrium), the precursor for the ligand is converted into the ligand such that binding occurs between the ligand and the binder species.

Subsequently, the second analyte binding species is introduced such that the second analyte binding species may bind with analyte species, if any, bound to the first analyte binding species which is attached, indirectly, to the support material.

In this example, in the presence of analyte species, tracer species (which is conjugated to the second analyte binding species) will become associated with the support material; increasing concentrations of analyte species in a sample may be shown by increased amounts of tracer species on the support material.

In the absence of analyte species, substantially no tracer species will be associated with the support material.

By use of calibration curves, obtained using a range of samples containing known amounts of standard analyte species, the amount of analyte species in an "unknown" sample may be determined.

The present invention will now be further described, by way of example, with reference to a competitive immunoassay.

The reagents involved may be as follows:

(a) a binder for an analyte species (being a purified primary antibody) labelled with a suitable tracer species (e.g. an enzyme), (b) a support material carrying a first auxiliary species (being a precursor for a second auxiliary species comprising a ligand (e.g. a hapten)), (c) authentic analyte species conjugated to a third species, in this example a third auxiliary species, (being a purified antibody to the ligand), and (d) a standard analyte species.

Reagent (b) is in excess and reagents (a) and (c) are present in "limited" quantities such that, upon combining the reagents, reagent (d) competes with reagent (c) for binding to the binder of reagent (a).

When this reaction, the primary immune reaction, has progressed to the chosen extent reagent (b) is treated so as to form the second auxiliary species from the first auxiliary species such that all, or a substantial proportion, of reagent (c) and complexes associated with it are bound with (b).

After removal of soluble unbound materials the tracer species (e.g. enzyme) activity associated with (b) may be measured as being inversely proportional to the amount of (d).

By way of example, a calibration curve may be established by repeating the competitive immunoassay immediately hereinbefore described with various quantities of standard analyte species. Thus, for example, the quantities of standard analyte species may be varied from zero to the maximum level covering the range required for a particular assay.

Maximum tracer species activity on the support material will be found at zero level of standard analyte species and this activity will decrease with increasing amounts of standard analyte species.

By replacing reagent (d) with a sample containing an unknown quantity of analyte species and repeating the immunoassay immediately hereinbefore described the amount of analyte species in the sample may be determined by use of the calibration curve.

The support material used in the immunoassay immediately hereinbefore described may be, for example, magnetisable particles or a surface of a reaction vessel.

By way of example, it is to be understood that a sensor in accordance with the present invention may, if desired, be such as to be reusable; this may be achieved, for example, by arranging for the second auxiliary species to be capable of being converted back into the first auxiliary species after a first immunoassay has been completed so as to permit a second immunoassay to be carried out.

It is to be understood that the term "immunological detection" as used in this Specification embraces, for example, any form of detection or analysis which involves an immunochemical interaction.

Where it is desired to prepare an antibody for use in accordance with the present invention (e.g. an antibody to a chosen ligand) such an antibody may be prepared by any suitable method, for example, those known for the raising of polyclonal or monoclonal antibodies; thus, antibodies may be raised, for example, by immunising animals with conjugates made of suitable derivatives of ligands and immunogenic carrier proteins such as bovine serum albumin or key-hole limpit haemocyanin; the product obtained by immunising animals may be purified as desired (e.g. by the use of affinity chromatography) to obtain the required antibodies.

The term "antibody" as used in this Specification embraces whole antibody or antibody fragments such as Fab and $(Fab)_2$ and, accordingly, the term "antibodies" used herein embraces whole antibodies and antibody fragments.

By way of example, a washing step or steps may be used, if desired, when effecting an immunoassay in accordance with the present invention.

DETAILED DESCRIPTION OF THE PREFERRED EMBODIMENTS

The present invention will now be further described by way of example, as follows:

EXAMPLE 1
Preparation of 7-hydroxy-4-methyl coumarin-3-propionic acid

In accordance with this Example 7-hydroxy-4-methyl coumarin-3-propionic acid was prepared as an example of a ligand for use as a second auxiliary species in accordance with the present invention.

Thus, 7-hydroxy-4-methyl coumarin-3-propionic acid ethyl ester was prepared by condensing resorcinol (11 g) and diethyl 2-acetyl glutarate (23 g) in concentrated sulphuric acid (50 ml). After 24 hr standing at room temperature the resulting reaction mixture was poured into 2 L of cold distilled water thereby to form a creamy-white precipitate. The creamy-white precipitate was washed with distilled water (4 L) and collected as an intermediate product. Thin layer chromatography on silica plates showed the intermediate product to be highly pure.

7-hydroxy-4-methyl coumarin-3-propionic acid was prepared from the intermediate product by removing ethyl ester with potassium hydroxide in methanol (5%). The final product was isolated by standard acid-base precipitation-dissolving procedures.

EXAMPLE 2
Preparation of antiserum to 7-hydroxy-4-methyl coumarin-3-propionic acid In accordance with this Example an antibody was prepared, said antibody being an antibody to the ligand prepared as in Example 1. The antibody was prepared for use as a third species in accordance with the present invention.

Thus, a sample of the final product prepared as in Example 1 (0.48 g) was first dissolved in tetra hydrofuran (THF) (24 ml) and then N-hydroxysuccinimide (0.24 g) was added followed by dicyclohexyl carbodiimide (0.41 g). After 24 hr standing, the resulting product, which was 7-hydroxy-4-methyl coumarin-3-propionic acid-N-hydroxy-succinimide ester, was used without further purification. An immunogen was prepared by coupling the ester (prepared as immediately hereinbefore disclosed) to bovine serum albumin. Thus, 2 ml of a solution of the ester in THF (50 mg of ester) were added to BSA (80 mg) dissolved in 0.1M $NaHCO_3$ (10 ml; pH 8.6) and dioxane (6 ml). The resulting conjugate was dialysed against 3 changes of 4 L of 1% $NaHCO_3$ over 3 days.

Sheep were immunised with about 1.5 mg of the conjugate (which was an immunogen) using standard procedures. Antiserum showing high binding activity to 7-hydroxy-4-methyl coumarin-3-propionic acid was obtained after 9 months of repeated immunisation.

EXAMPLE 3
Titration of antibody binding activity of the antibody prepared as in Example 2

In order to assess the antibody activity of the antibody produced as in Example 2, a plate coating antigen reagent was prepared as follows:

An ovalbumin solution was prepared by dissolving ovalbumin (20 mg) in 0.1M $NaHCO_3$ (5 ml; pH 8.6) and dimethyl formamide (5 ml). N-hydroxysuccinimide ester (5 mg), as prepared in Example 2, was dissolved in dimethyl sulphoxide (0.5 ml) and the resulting solution was added to the ovalbumin solution. The resulting mixture was thoroughly mixed and left to stand for 24 hr.

The resulting plate coating antigen reagent (which was a conjugate material) was purified by dialysis for 3 days against 3 changes of 4 L of 1% $NaHCO_3$ followed by treatment with 1% activated Norit A charcoal.

Titration of antibody binding activity of the antibody prepared as in Example 2 was carried out using ELISA.

Thus, binding activity was assessed by ELISA as follows:
Microtitre ELISA plates (polystyrene) were coated with plate coating antigen reagent prepared as immediately hereinbefore disclosed. Thus, 150 μl of plate coating antigen reagent in 1% $NaHCO_3$ (0. 5 μg/ml plate coating antigen reagent) were added to each well of the plates and the plates were left to stand at 4° C. overnight. Excess sites were blocked with 0.5 mg/ml horse haemoglobin solution (200

μl). Serial dilutions of the antiserum (prepared as in Example 2) were made in assay buffer (50 mM Tris-HCl buffer, pH 7.4, containing 0.1M NaCl, 0.1% gelatin, 0.01% Thimerosal and 0.1 mg/ml of rhodamine B base).

The titration assay was effected by adding 150 μl of antiserum (various dilutions, range: 1/100 to 1/10$^6$), shaking for 1 hr at room temperature, washing (×3) with wash buffer (consisting of 0.1M NaHCO$_3$ solution containing 0.1M NaCl and 0.05% Tween 20) and adding a developing second antibody-enzyme conjugate (comprising rabbit anti-sheep IgG-HRP), incubating at 37° C. for 1 hr, washing (×3) with wash buffer, and then adding HRP substrate and chromogen solution (1.3 mM H$_2$O$_2$ in citrate-sodium acetate buffer pH 4.1 containing 0.5 mg/ml ABTS). Optical density at 415 nm was read in a microtitre plate ELISA reader after 20 min reaction with the substrate.

The antibody titre was found to be 1/380,000 (i.e. the dilution of antiserum which gave an ELISA Optical Density (O.D.) of 1.7 at 415 nm).

EXAMPLE 4

Preparation of precursor for 7-hydroxy-4-methyl coumarin-3-propionic acid

In accordance with this Example, a precursor was prepared for the ligand prepared in Example 1. The precursor was for use as a first auxiliary species in accordance with the present invention.

The precursor was β-galactopyranoside-o-(4-methyl coumarin-3-propionic acid).

Thus, tetraacetyl-α-D-galactopyranosyl bromide (5 g) was added to a solution of 7-hydroxy-4-methyl coumarin-3-propionic acid ethyl ester (0.75 g) in acetone (50 ml) with 0.5 g of anhydrous potassium carbonate. The resulting mixture was refluxed for 10 hr to give a post-reaction mixture. The product, the tetraacetyl galactopyranoside derivative of 7-hydroxy-4-methyl coumarin-3-propionic acid ethyl ester, was isolated by standard extraction steps. Thus, chloroform (300 ml) solution of the post-reaction mixture was washed repeatedly with 0.5M sodium hydroxide until all traces of starting materials were removed from the chloroform layer. The product was recovered from the chloroform layer. The acetyl groups and the ethyl ester were removed by 5% potassium hydroxide in methanol.

Thus the tetraacetyl-β-D-galactopyranoside-o-(4-methyl coumarin-3-propionic acid ethyl ester (0.7 g) was left for 16 hr at 50° C. in 40 ml of 5% potassium hydroxide in methanol.

The free glycoside product was recovered and purified by preparative liquid chromatography on silica gel plates.

Cross-reaction of β-D-galactopyranoside-o-(4-methyl coumarin-3-propionic acid) with anti-7-hydroxy-4-methyl coumarin-3-propionic acid antiserum was assessed using competitive ELISA.

Taking the binding of 7-hydroxy-4-methyl coumarin-3-propionic acid with anti-7-hydroxy-4-methyl coumarin-3-propionic acid antiserum as 100% the cross-reaction of β-D-galactopyranoside-o-(4-methyl coumarin-3-propionic acid) with the antiserum was found to be 0.016%.

EXAMPLE 5

Coupling of β-D-galactopyranoside-o-(4-methyl coumarin-3-propionic acid) to dextran Dextran was activated as follows:

Dextran (ex. Sigma; MW 500,000) (2 g) in 1% NaHCO$_3$ (50 ml) was oxidised with sodium periodate (0.25 g). The resulting mixture was left to stand in the dark for 6 hr and then was dialysed against 4 L distilled water for 16 hr at 4° C. Oxidation of dextran with sodium periodate introduces aldehyde functions into the dextran structure. Aldehyde groups react with free amino groups to form covalent links. The covalent links may be stabilised by reduction with sodium borohydride.

Link arms were introduced onto the oxidised dextran as follows:

Oxidised dextran (0.5 g) in 0.1M NaHCO$_3$ (25 ml; pH 7.4) was reacted with bis(hexa methylene) triamine (H$_2$N—(CH$_2$)$_6$—NH—(CH$_2$)$_6$—NH$_2$) (0.25 g). The pH of the resulting reaction mixture was adjusted to 7.2 with concentrated HCl and the reaction mixture was stirred at room temperature for 24 hr. Sodium borohydride (0.2 g) was added and after mixing for 4 hr the resulting mixture was dialysed against 1% NaHCO$_3$ to remove low MW materials.

The coupling of β-D-galactopyranoside-o-(4-methyl coumarin-3-propionic acid) to dextran was carried out as follows:

The β-D-galactopyranoside-o-(4-methyl coumarin-3-propionic acid) was converted to β-D-galactopyranoside-o-(4-methyl coumarin-3-propionic acid)-N-hydroxysuccinimide ester. Thus, β-D-galactopyranoside-o-(4-methyl coumarin-3-propionic acid) (0.4 gm) was dissolved in methanol (20 ml) and dioxane (30 ml). Subsequently N-hydroxysuccinimide (0.12 g) and dicyclohexyl carbodiimide (0.22 g) were added. The resulting reaction mixture was left to stand in the cold for at least 7 days. A sample of the ester thus produced (100 mg) was added to dextran-NH—(CH$_2$)$_6$—NH—(CH$_2$)$_6$—NH$_2$, prepared as hereinbefore disclosed in this Example, (200 mg) in 0.1M NaHCO$_3$ (10 ml; pH 8.6). The resulting further reaction mixture was allowed to react and twenty-four hours later a hapten derivative was added as disclosed further in Example 6.

EXAMPLE 6

Preparation of dextran for attachment to a polystyrene surface

Although some carrier materials (such as dextran) may be suitable hydrophillic materials (e.g. polymers) to which, for example, ligands or a ligand precursor may be linked, some carrier materials (such as dextran) do not adsorb satisfactorily to polystyrene surfaces (e.g. such as those found on polystyrene microtitre plates).

However, such carrier materials (e.g. dextran) may be, for example, attached to a polystyrene surface by any suitable covalent linkage via an adsorbing protein.

Alternatively, by way of example, such carrier materials (e.g. dextran) may be attached to a surface (e.g. a polystyrene surface) by means of a ligand species-binder species pair. Thus, for example, a binder species (comprising an antibody) may be adsorbed onto a surface and a ligand species for the binder species may be attached to a carrier material (e.g. dextran).

In this Example, a plurality of ligands, each ligand comprising 5(6)-carboxy fluorescein, were attached to dextran-NH—(CH$_2$)$_6$—NH—(CH$_2$)$_6$—NH$_2$.

Thus, after 24 hours a hapten derivative comprising 5(6)-carboxy fluorescein-N-hydroxysuccinimide (10 mg) was added to the mixture formed by allowing the further reaction mixture disclosed in Example 5 to react and the resulting mixture was left for 4 hr. The post-reaction mixture thus produced was dialysed for 3 days in the cold to remove low MW substances and final purification was carried out by treatment with 1% Norit A activated charcoal.

The ratio of β-D-galactopyranoside-o-(4-methyl coumarin-3-propionic acid) entities to 5(6)-carboxy fluorescein entities attached to the dextran may be conveniently, for example, greater than 1:1 and may be conveniently, for example, 100:1.

EXAMPLE 7
Purification of antibody prepared as in Example 2

The IgG fraction of antiserum (prepared as in Example 2) was prepared by ion exchange chromatography.

Purification was carried out using immunoaffinity chromatography. An immunoadsorbent for this immunoaffinity chromatography was prepared by coupling a 7-amino-4-methyl coumarin-3-acetic acid-ovalbumin conjugate to cyanogen bromide activated Sepharose 4B. After contacting the antiserum with the immunosorbent antibodies bound to the immunoadsorbent were eluted with a gradient of 20% acetonitrile and 1% propionic acid in distilled water. The antibody thus eluted was dialysed against 0.05M Na phosphate buffer (pH 7.0), containing 0.1M NaCl.

Titration of binding activity by ELISA showed that the resulting antibody has high titre. An O.D. (at 415 nm) of 1.7 was obtained by 0.5 ng of the antibody.

EXAMPLE 8
Preparation of a conjugate of 17β-estradiol and anti-7-hydroxy-4-methyl coumarin-3-propionic acid antibody 170β-estradiol was selected as an analyte species to illustrate, by way of example, detection in accordance with the present invention.

A conjugate of 17β-estradiol and anti-7-hydroxy-4-methyl coumarin-3-propionic acid antibody was prepared.

Thus, 17β-estradiol-3-o-carboxybutyryl ether-N-hydroxysuccinimide ester (0. 15 mg) in dioxane (75 μl) was added to antibody (IgG fraction) prepared as in Example 7 (12 mg) in 0.1M NaHCO$_3$ (4 ml; pH 8.6) containing 0.1M NaCl.

After standing for 4 hr, the resulting reaction mixture was treated with 0.5% Norit A charcoal and the resulting solution was dialysed overnight in the cold against 50 mM Na phosphate (pH 7.4).

EXAMPLE 9
Preparation of anti-17β-estradiol antibody

Rabbit anti-17β-estradiol antiserum was raised against an immunogen being a conjugate of 17β-estradiol-3-carboxymethyl ether and KLH (keyhole limpit haemocyanin) by immunisation over a period of 7 months.

The antiserum was recovered by standard methods.

EXAMPLE 10
Preparation of anti-5(6)-carboxy fluorescein antibody

Sheep anti-fluorescein antiserum was raised against an immunogen being a conjugate of 5(6)-carboxy fluorescein and KLH by immunisation over a period of 7 months.

The IgG fraction of sheep antiserum was isolated by ion exchange chromatography.

The IgG antibody was recovered and purified by immunoaffinity chromatography.

An immunoadsorbent for this immunoaffinity chromatography was prepared by coupling 2',7'-dichloro-5(6)-carboxy fluorescein-ovalbumin conjugate to hydrogen bromide activated Sepharose 4B.

After contacting the antiserum with the immunosorbent, antibody bound by the immunosorbent was eluted by a gradient of 20% acetonitrile and 1% propionic acid in distilled water. Eluted antibody was dialysed in the cold for 3 days against 50 mM Na phosphate (pH 7.0) containing 0.1M NaCl.

EXAMPLE 11
17β-estradiol enzyme immunoassay using a first auxiliary species, a second auxiliary species and a third species In this Example the first auxiliary species is β-D-galactopyranoside-o-(4-methyl coumarin-3-propionic acid) which is capable of being formed into a second auxiliary species which is 7-hydroxy-4-methyl coumarin-3-propionic acid.

The third species in this Example is an antibody to 7-hydroxy-4-methyl coumarin-3-propionic acid.

Support material (in the form of polystyrene microtitre plates) was coated with 5(6)-carboxy fluorescein antibody. Thus, polystyrene microtitre plates were coated with purified 5(6)-carboxy fluorescein antibody (IgG fraction) prepared as in Example 10.

To achieve this, antibody (IgG fraction) prepared as in Example 10 was introduced to the plates by putting 150 μl of a solution containing the antibody into wells of the microtitre plates. The solution was made up of 10 μg/ml antibody in PBS (0.01M sodium phosphate (pH 7.4) containing 0.9% NaCl).

The solution was left for 16 hours at 4° C. and then the wells were emptied and excess sites were blocked by exposing the wells to horse haemoglobin for 1 hour (200 μl per well of a solution of 0.5 mg/ml horse haemoglobin in 1% NaHCO$_3$ solution).

Subsequently dextran, having first auxiliary species and having a plurality of ligands comprising 5(6)-carboxy fluorescein, (prepared as hereinbefore disclosed), was introduced to the wells so that the dextran could become attached to the plates by means of binding between the antibody on the plates and the ligands of the dextran.

Thus, 150 μl of a solution of dextran (associated with the first auxiliary species and with the 5(6)-carboxy fluorescein ligands), prepared as in Example 6, in assay buffer (5 μg/ml) was introduced to wells of the microtitre plates and left for 30 mins with shaking to permit attachment of the dextran to the plates. The assay buffer was as disclosed in Example 3. The plates were washed four times with wash buffer; the wash buffer was as in Example 3.

Subsequently a blank (50 μl) (consisting of assay buffer containing no 17β-estradiol) and 17β-estradiol standards (each 50 μl) containing 17β-estradiol in assay buffer (at concentrations of 10 pg to 250 pg 17β-estradiol per 50 μl of assay buffer) were introduced into the wells (in duplicate).

Also to each well was added 50 μl of a solution consisting of conjugate prepared as in Example 8 suitably diluted in assay buffer (in accordance with immunoassay procedures to 1/8000) and 50 μl of a solution of rabbit anti-17β-estradiol antibody prepared as in Example 9 suitably diluted in assay buffer (in accordance with immunoassay procedures to 1/18,000).

It will be appreciated that at this point a primary immune reaction was taking place with 17β-estradiol (if present) competing with the conjugate prepared as in Example 8 for binding with the antibody prepared as in Example 9.

After mixing (by shaking the plates) for 20 min a reagent was added in order to effect conversion of the first auxiliary species into the second auxiliary species (i.e. in this Example conversion of β-D-galactopyranoside-o-(4-methyl coumarin-3-propionic acid) to 7-hydroxy-4-methyl coumarin-3-propionic acid).

The reagent for effecting this conversion was an *E. coli* β-D-galactosidase preparation (ex. Sigma) (0.5 unit in assay buffer) with added MgCl$_2$ (10 μM) and methanol (15%) v/v); 50 μl of the reagent were added to each well.

After shaking the plates for 20 mins, the plates were washed six times with wash buffer. At this point the conjugate as prepared in Example 8 (together with any rabbit anti-17β-estradiol antibody attached thereto) will become attached to the plates by binding occurring between the anti-7-hydroxy-4-methyl coumarin-3-propionic acid antibody and the 7-hydroxy-4-methyl coumarin-3-propionic acid ligand formed by enzymatic action upon β-D-galactopyranoside-o-(4-methyl coumarin-3-propionic acid).

Subsequently commercially available second antibody-enzyme conjugate (goat anti-rabit-HRP conjugate (Sigma)) was added (150 μl per well) and left to react with any anti-17β-estradiol antibody attached to the plates.

The plates were washed with wash buffer and any assay signal was developed by use of HRP substrate (150 μl per well) consisting of 1.3 mM $H_2O_2$ in acetate/citrate buffer (pH 4.1) containing 0.5 mg per ml ABTS.

The results are given in the following Table in which the O.D. (Optical Density) results are the average of two readings.

TABLE

| Concentration of 17β-estradiol (pg) | O.D. (at 415 nm) |
|---|---|
| 0 | 1.30 |
| 10 | 1.10 |
| 25 | 0.80 |
| 50 | 0.55 |
| 100 | 0.35 |
| 250 | 0.06 |

The results given in the Table confirm that as the concentration of analyte species (in this Example 17β-estradiol) increases the amount of primary antibody which may be associated with a support material decreases.

I claim:

1. In an immunoassay method to determine the presence or concentration of an analyte in a sample wherein a primary species capable of specific binding to said analyte is brought into contact with the sample in an immune reaction mixture and then separated from the reaction mixture by linkage to a support which is then removed or isolated from the mixture, the improvement consisting of causing the primary species to become linked to the support by the steps of:
   (a) causing a first auxiliary species not capable of undergoing specific binding with a third species to react with an enzyme to expose an antigenic ligand of said first species and thereby convert it into a second auxiliary species capable of undergoing specific immunological binding with said third species;
   (b) causing the second auxiliary species and the third species to undergo a specific immunological binding interaction, one of the first auxiliary species, the second auxiliary species and the third species being capable of becoming linked to the support, and another of the first auxiliary species, the second auxiliary species and the third species being capable of becoming linked to the primary species and
   causing the species capable of becoming linked to the support to become linked to the support and causing the species capable of becoming linked to the primary species to become linked to the primary species.

2. In an immunoassay method to determine the presence or concentration of an analyte in a sample wherein a tracer species is added to the sample and caused to become associated with any analyte present and a primary species capable of specific binding to said analyte is brought into contact with the sample in an immune reaction mixture and then separated from the reaction mixture by linkage to a support which is then removed or isolated from the mixture, the improvement consisting of detecting the amount of the analyte in the sample by the steps of:
   (a) causing a first auxiliary species not capable of undergoing specific binding with a third species to react with an enzyme to expose an antigenic ligand of said first species and thereby convert it into a second auxiliary species capable of undergoing specific immunological binding with said third species;
   (b) causing the second auxiliary species and the third species to undergo a specific immunological binding interaction, one of the first auxiliary species, the second auxiliary species and the third species being capable of becoming linked to the support, and another of the first auxiliary species, the second auxiliary species and the third species being capable of becoming linked to the primary species;
   c) causing the species capable of becoming linked to the support to become linked to the support, and causing the species capable of becoming linked to the primary species to become linked to the primary species, thereby causing the primary species to become associated with the support;
   (d) bringing the primary species associated with the support into contact with the reaction mixture;
   (e) separating the support from the reaction mixture; and
   (f) calculating the amount of the analyte in the sample by detecting the amount of the tracer species associated with the support.

3. In an immunoassay method to determine the presence or concentration of an analyte in a sample, wherein an analyte analog is brought into contact with the sample in an immune reaction mixture and the analyte analog and any analyte present compete for linkage to a support which is subsequently separated from the reaction mixture, the improvement consisting of a method of causing the analyte and analyte analog to become linked to the support by:
   (a) causing a first auxiliary species not capable of undergoing specific binding with a third species to react with an enzyme to expose an antigenic ligand of said first species and thereby convert it into a second auxiliary species capable of undergoing specific immunological binding with said third species, one of the first auxiliary species, the second auxiliary species and the third species being linked to the support and another of said species being capable of becoming linked to the analyte and the analyte analog;
   (b) causing the second auxiliary species and the third species to undergo a specific immunological binding interaction;
   (c) bringing the support and the analyte analog into contact with the sample; and
   (d) causing the species capable of becoming linked to the analyte and to the analyte analog to become linked thereto,
thereby effecting linkage of the analyte and the analyte analog to the support.

4. In an immunoassay method to determine the presence or concentration of an analyte in a sample, wherein an analyte analog is brought into contact with the sample in an immune reaction mixture and the analyte analog and any analyte present compete for linkage to a support which is subsequently separated from the reaction mixture, the improvement consisting of a method of detecting the amount of the analyte in the sample by:
   (a) causing a first auxiliary species not capable of undergoing specific binding with a third species to react with an enzyme to expose an antigenic ligand of said first species and thereby convert it into a second auxiliary species capable of undergoing specific immunological binding with said third species;

(b) causing the second auxiliary species and the third species to undergo a specific immunological binding interaction, one of the first auxiliary species and the second auxiliary species being linked to the support, and the third species being capable of becoming linked to the analyte and the analyte analog;

(c) bringing the analyte analog and the support into contact with the sample in an immune reaction mixture, said analyte analog having a tracer species associated therewith;

(e) separating the support from the mixture; and (f) calculating the amount of the analyte in the sample by detecting the amount of the tracer species associated with the support.

5. In an immunoassay method to determine the presence or concentration of an analyte in a sample wherein a species capable of specific immunological binding to said analyte is brought into contact with the sample in an immune reaction mixture and then separated from the reaction mixture by linkage to a support which is then removed or isolated from the mixture, the improvement consisting of the steps of:

(a) causing a first auxiliary species, which is linked to the support and is not capable of undergoing specific binding with a third species, to react with an enzyme to expose an antigenic ligand of said first species and thereby convert it into a second auxiliary species capable of undergoing specific immunological binding with said third species; and (b) causing the second auxiliary species and the third species to undergo a specific immunological binding interaction, said third species also having a primary function capable of undergoing a specific binding interaction with the analyte, thereby effecting linkage of the third species to the support.

6. In an immunoassay method to determine the presence or concentration of an analyte in a sample, wherein (i) a primary species capable of specific immunological binding to said analyte and to an analyte analog and (ii) said analyte analog a brought into contact with the sample in an immune reaction mixture and the analyte analog and any analyte present compete for specific immunological binding to the primary species, the improvement consisting of a method of detecting the amount of the analyte in the sample by:

(a) causing a first auxiliary species, which is linked to the support and is not capable of undergoing specific binding with a third species, to react with an enzyme to expose an antigenic ligand of said first species and thereby convert it into a second auxiliary species capable of undergoing specific immunological binding with said third species; and (b) causing the second auxiliary species and the third species to undergo a specific binding interaction, said third species a having a primary function capable of undergoing a specific binding interaction with the analyte and the analyte analog;

(c) bringing the analyte analog and the support into contact with the sample in an immune reaction mixture and allowing any analyte present in the sample to compete with the analyte analog for specific binding to the primary function of the third species, said analyte analog having a tracer species associated therewith;

(d) separating the support from the mixture; and (e) detecting the amount of the tracer species associated with the support.

7. A method as claimed in claims 5 or 6 wherein the third species is a bifunctional antibody having a first function capable of undergoing a specific immunological binding interaction with the second species and a second function capable of undergoing a specific immunological binding interaction with the analyte and the analyte analog.

8. In an immunoassay method to determine the presence or concentration of an analyte in a sample wherein a primary species capable of competing with said analyte is brought into contact with the sample in an immune reaction mixture and then separated from the reaction mixture by linkage to a support which is then removed or isolated from the mixture, the improvement consisting of causing the primary species to become linked to the support by the steps of:

(a) causing a first auxiliary species not capable of undergoing specific binding with a third species to react with an enzyme to expose an antigenic ligand of said first species and thereby convert it into a second auxiliary species capable of undergoing specific immunological binding with said third species;

(b) causing the second auxiliary species and the third species to undergo a specific immunological binding interaction, one of the first auxiliary species, the second auxiliary species and the third species being capable of becoming linked to the support, and another of the first auxiliary species, the second auxiliary species and the third species being capable of becoming linked to the primary species; and (c) causing the species capable of becoming linked to the support to become linked to the support, and causing the species capable of becoming linked to the primary species to become linked to the primary species.

9. In an immunoassay method to determine the presence or concentration of an analyte in a sample wherein (i) a tracer species is added to the sample and caused to become associated with any analyte present, and (ii) a primary species capable of competing with said analyte is brought into contact with the sample in an immune reaction mixture and then separated from the reaction mixture by linkage to a support which is then removed or isolated from the mixture, the improvement consisting of detecting the amount of the analyte in the sample by the steps of:

(a) causing a first auxiliary species not capable of undergoing specific binding with a third species to react with an enzyme to expose an antigenic ligand of said first species and thereby convert it into a second auxiliary species capable of undergoing specific immunological binding with said third species;

(b) causing the second auxiliary species and the third species to undergo a specific immunological binding interaction, one of the first auxiliary species, the second auxiliary species and the third species being capable of becoming linked to the support, and another of the first auxiliary species, the second auxiliary species and the third species being capable of becoming linked to the primary species;

(c) causing the species capable of becoming linked to the support to become linked to the support and causing the species capable of becoming linked to the primary species to become linked to the primary species, thereby causing the primary species to become associated with the support;

(d) separating the support from the reaction mixture; and (e) calculating the amount of the analyte in the sample by detecting the amount of the tracer species associated with the support.

10. In an immunoassay method to determine the presence or concentration of an analyte in a sample wherein (i) a primary species capable of competing with said analyte, said primary species having a tracer species associated therewith, and (ii) a support are brought into contact with the sample in an immune reaction mixture and the support is subsequently separated from the reaction mixture, the improvement consisting of a method of detecting the amount of the analyte in the sample by:

(a) causing a first auxiliary species not capable of undergoing specific binding with a third species to react with an enzyme to expose an antigenic ligand of said first species and thereby convert it into a second auxiliary species capable of undergoing specific immunological binding with said third species;

(b) causing the second auxiliary species and the third species to undergo a specific immunological binding interaction, one of the first auxiliary species, the second auxiliary species and the third species being capable of becoming linked to the support, and another of the first auxiliary species, the second auxiliary species and the third species being capable of becoming linked to the primary species; and (c) causing the species capable of becoming linked to the support to become linked thereto, and causing the species capable of becoming linked to the primary species to become linked thereto, thereby effecting linkage of the primary species to the support; and (d) detecting the amount of the tracer species associated with the support.

11. A test apparatus for use in an immunoassay performed to determine the presence or concentration of an analyte in a sample, comprising:

(a) a support;

(b) a first auxiliary species not capable of undergoing a specific binding interaction with a third species but which is capable of reacting with an enzyme to expose an antigenic ligand of said first species and thereby convert it into a second auxiliary species capable of undergoing a specific immunological binding interaction with said third species; and (c) the third species, one of the first auxiliary species, the second auxiliary species and the third species being capable of becoming linked to the support, and another of the first auxiliary species, the second auxiliary species and the third species being capable of becoming linked to the analyte or to a primary species capable of undergoing a specific binding interaction with the analyte.

12. A test-kit for use in an immunoassay performed to determine the presence or concentration of an analyte in a sample, comprising:

(a) a support;

(b) a first auxiliary species not capable of undergoing a specific binding interaction with a third species but which is capable of reacting with an enzyme to expose an antigenic ligand of said first species and thereby convert it into a second auxiliary species capable of undergoing a specific immunological binding interaction with said third species;

(c) the third species; and (d) a primary species capable of undergoing a specific binding interaction with the analyte, one of the first auxiliary species, the second auxiliary species and the third species being capable of becoming linked to the support and another of the first auxiliary species, the second auxiliary species and the third species being capable of becoming linked to the primary species.

13. A test apparatus for use in an immunoassay performed to determine the presence or concentration of an analyte in a sample, comprising:

(a) a support;

(b) a first auxiliary species not capable of undergoing a specific binding interaction with a third species but which is capable of reacting with an enzyme to expose an antigenic ligand of said first species and thereby convert it into a second auxiliary species capable of undergoing a specific immunological binding interaction with said third species; and (c) the third species, one of the first auxiliary species, the second auxiliary species and the third species being capable of becoming linked to the support, and another of the first auxiliary species, the second auxiliary species and the third species being capable of becoming linked to the analyte and to a primary species which competes with the analyte.

14. A test-kit for use in an immunoassay performed to determine the presence or concentration of an analyte in a sample, comprising:

(a) a support;

(b) a first auxiliary species not capable of undergoing a specific binding interaction with a third species but which is capable of reacting with an enzyme to expose an antigenic ligand of said first species and thereby convert it into a second auxiliary species capable of undergoing a specific immunological binding interaction with said third species;

(c) the third species; and (d) a primary species which competes with the analyte, one of the first auxiliary species, the second auxiliary species and the third species being capable of becoming linked to the support, and another of the first auxiliary species, the second auxiliary species and the third species being capable of becoming linked to the primary species and to the analyte.

15. A method as claimed in claims 1, 2, 3, 4, 5, 6, 8, 9, 13, 14 or 10 wherein the support is selected from the group consisting of a surface of a reaction vessel, an insoluble polysaccharide, a microparticle, an insoluble polysaccharide with entrapped iron oxide, polystyrene, cross-linked dextran, an insoluble polymer structure, a glass surface, a derivatized silica surface, a soluble polymer attached to a suitable surface, nylon, and a polyamide.

16. A method as claimed in claims 1, 2, 3, 4, 5, 6, 8, 9, 13, 14 or 10 wherein the analyte is selected from the group consisting of a hormone, a steroid, a drug, a polypeptide hormone, a tumor marker, a protein antigen, a blood protein, a marker protein, a pesticide, a toxin, a micro-organism and an antibody to a micro-organism.

* * * * *